United States Patent
Lee

(10) Patent No.: US 9,744,030 B2
(45) Date of Patent: Aug. 29, 2017

(54) CAPSULAR RING WITH IMPROVED FIXATION AND CENTERING

(71) Applicant: NOVARTIS AG, Basel (CH)

(72) Inventor: Sung Kyu Lee, Euless, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/833,410

(22) Filed: Aug. 24, 2015

(65) Prior Publication Data
US 2016/0220354 A1 Aug. 4, 2016

Related U.S. Application Data

(60) Provisional application No. 62/111,729, filed on Feb. 4, 2015.

(51) Int. Cl.
*A61F 2/14* (2006.01)
*A61F 2/16* (2006.01)

(52) U.S. Cl.
CPC .............. *A61F 2/1694* (2013.01); *A61F 2/15* (2015.04); *A61F 2002/1681* (2013.01); *A61F 2220/0008* (2013.01); *A61F 2230/0065* (2013.01)

(58) Field of Classification Search
CPC ........ A61F 2/16; A61F 2/1648; A61F 2/1613; A61F 2/1629; A61F 2/1602; A61F 2/14; A61F 2/147; A61F 2/1635; A61F 2/1694; A61F 2002/169
See application file for complete search history.

(56) References Cited

U.S. PATENT DOCUMENTS

| | | | | |
|---|---|---|---|---|
| 4,073,014 A | * | 2/1978 | Poler | ........................ A61F 2/16 623/6.41 |
| 4,326,306 A | * | 4/1982 | Poler | ..................... A61F 2/1662 206/205 |
| 5,843,184 A | * | 12/1998 | Cionni | .................. A61F 2/1694 623/4.1 |

(Continued)

FOREIGN PATENT DOCUMENTS

FR  2770394  *  7/1999

OTHER PUBLICATIONS

PCT/US2015/046491; International Search Report, International Searching Authority, Nov. 23, 2015, 2 pages.

*Primary Examiner* — David H Willse
*Assistant Examiner* — Tiffany Shipmon

(57) ABSTRACT

A capsular ring includes substantially circular anterior and posterior surfaces each defining a central void of the capsular ring, at least a portion of the anterior and posterior surfaces being substantially flat. The capsular ring further includes an exterior surface extending around the circumference of the capsular ring between the anterior surface and the posterior surface, wherein there is a sharp transition between the exterior surface and both the anterior surface and the posterior surface. The capsular ring further includes a plurality of orifices spaced circumferentially around the exterior surface and a plurality of haptics spaced circumferentially around the exterior surface and extending outwardly from the capsular ring; each of the plurality of haptics being configured, upon insertion of the capsular ring into a capsular bag of a patient's eye, to engage an equatorial region of the capsular bag of the patient's eye.

5 Claims, 6 Drawing Sheets

(56) References Cited

U.S. PATENT DOCUMENTS

| | | | |
|---|---|---|---|
| 8,585,759 B2 * | 11/2013 | Bumbalough | A61F 2/1613 623/6.37 |
| 9,095,424 B2 | 8/2015 | Kahook et al. | |
| 9,125,736 B2 | 9/2015 | Kahook et al. | |
| 9,289,287 B2 | 3/2016 | Kahook et al. | |
| 9,364,316 B1 | 6/2016 | Kahook et al. | |
| 9,387,069 B2 | 7/2016 | Kahook et al. | |
| 9,421,088 B1 | 8/2016 | Kahook et al. | |
| 2003/0050695 A1 | 3/2003 | Lin et al. | |
| 2004/0039446 A1 | 2/2004 | McNicholas | |
| 2005/0015144 A1 * | 1/2005 | Tran | A61F 2/1613 623/6.41 |
| 2009/0222087 A1 | 9/2009 | Coroneo | |
| 2009/0248154 A1 | 10/2009 | Dell | |
| 2010/0204788 A1 | 8/2010 | Van Noy | |
| 2015/0230981 A1 | 8/2015 | Kahook et al. | |
| 2016/0235587 A1 | 8/2016 | Kahook et al. | |
| 2016/0278912 A1 | 9/2016 | Kahook et al. | |

\* cited by examiner

FIG. 4A
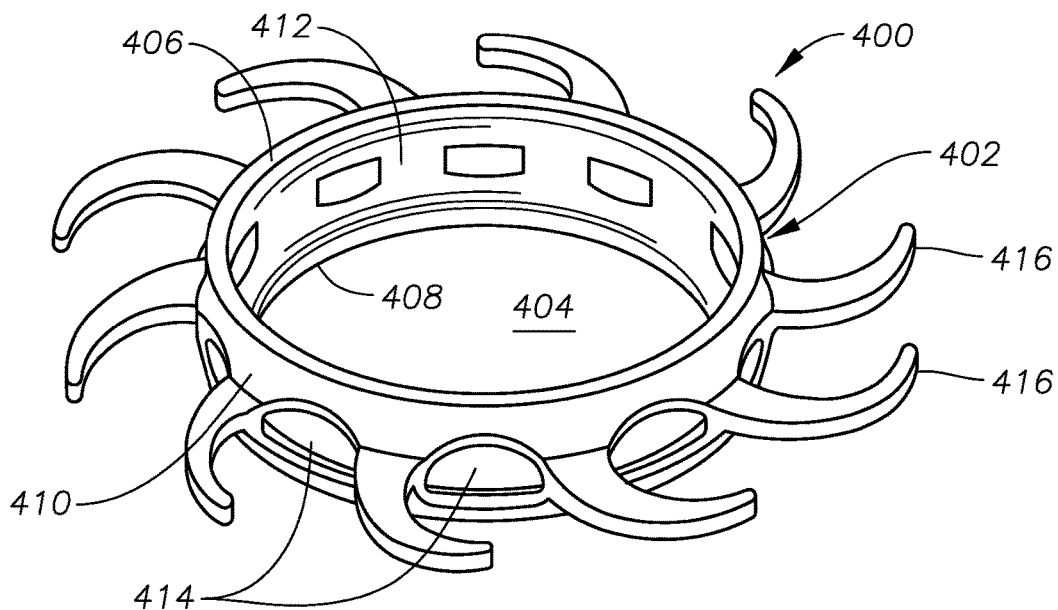
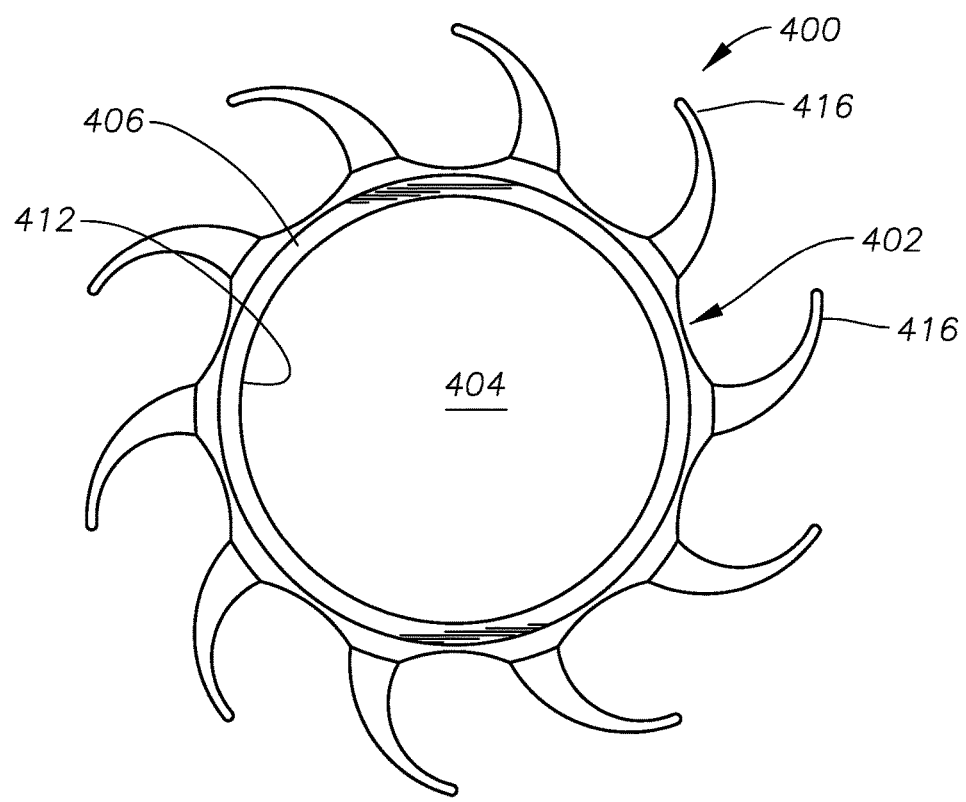
FIG. 4B

CAPSULAR RING WITH IMPROVED FIXATION AND CENTERING

This application claims the priority of U.S. Provisional Application No. 62/111,729 filed Feb. 4, 2015 which is hereby incorporated herein by reference in its entirety.

FIELD

This present disclosure relates generally to cataract surgery and, more particularly, to a capsular ring with improved fixation and centering.

BACKGROUND

Visually impairing cataract, or clouding of the lens, is the leading cause of preventable blindness in the world. Presently, cataracts are treated by surgical removal of the affected lens and replacement with an artificial intraocular lens ("IOL"). FIG. 1 is a diagram of an eye 100 illustrating anatomical structures related to the surgical removal of a cataract and the implantation of an IOL. The eye 100 comprises an opacified lens 102, an optically clear cornea 104, and an iris 106. A lens capsule (capsular bag 108) located behind the iris 106 of the eye 100 contains the opacified lens 102. More particularly, the opacified lens 102 is seated between an anterior capsule segment (anterior capsule 110) and a posterior capsular segment (posterior capsule 112). The anterior capsule 110 and the posterior capsule 112 meet at an equatorial region 114 of the capsular bag 108. The eye 100 also comprises an anterior chamber 116 located in front of the iris 106 and a posterior chamber 118 located between the iris 106 and the capsular bag 108.

A common technique for cataract surgery is extracapsular cataract extraction ("ECCE"), which involves the creation of an incision near the outer edge of the cornea 104 and an opening in the anterior capsule 110 (i.e., an anterior capsulotomy) through which the opacified lens 102 is removed. The lens 102 can be removed by various known methods. One such method is phacoemulsification, in which ultrasonic energy is applied to the lens to break it into small pieces that are aspirated from the capsular bag 108. Thus, with the exception of the portion of the anterior capsule 110 that is removed in order to gain access to the lens 102, the capsular bag 108 may remain substantially intact throughout an ECCE. The intact posterior capsule 112 provides a support for the IOL and acts as a barrier to the vitreous humor within the posterior chamber 120 of the eye 100. Following removal of the opacified lens 102, an artificial IOL, which may be designed to mimic the transparency and refractive function of a healthy lens, is typically implanted within the capsular bag 108 through the opening in the anterior capsule 110. The IOL may be acted on by the zonular forces exerted by a ciliary body 122 and attached zonules 124 surrounding the periphery of the capsular bag 108. The ciliary body 122 and the zonules 124 anchor the capsular bag 108 in place and facilitate accommodation, the process by which the eye 100 changes optical power to maintain a clear focus on an image as its distance varies.

A frequent complication of ECCE and other forms of cataract surgery is opacification of the posterior capsule 112. Posterior capsule opacification ("PCO") results from the migration of residual lens epithelial cells from the equatorial region 114 of the capsular bag 108 toward the center of the posterior capsule 112. One factor contributing to the development of PCO is contact between the IOL and the surface of the posterior capsule 112. Subsequent to ECCE, the lens epithelial cells may proliferate between the IOL and the surface of the posterior capsule 112, leading to wrinkling and clouding of the normally clear posterior capsule 112. If clouding of the posterior lens capsule 112 occurs within the visual axis, then the patient will experience a decrease in visual acuity and may require additional surgery to correct the patient's vision.

A widely utilized procedure to clear the visual axis of PCO is Neodymium: Yttrium-Aluminum-Garnet ("Nd/YAG") laser capsulotomy, in which a laser beam is used to create an opening in the center of the cloudy posterior capsule 112. However, Nd/YAG laser capsulotomy exposes patients to the risk of severe complications that can lead to significant visual impairment or loss, such as retinal detachment, papillary block glaucoma, iris hemorrhage, uveitis/vitritis, and cystoid macula edema. Moreover, the laser energy is ordinarily directed though the IOL, which may damage the optics of the implant or disrupt its placement within the capsular bag 108. Accordingly, there exists a need to prevent the occurrence of PCO rather than treating PCO at a later date after implantation of an IOL.

SUMMARY

In general, the present disclosure relates to an IOL system including a capsular ring designed to improve centration of the capsular ring in the capsular bag 108 as well as inhibit PCO. In certain embodiments, a capsular ring includes substantially circular anterior and posterior surfaces each defining a central void of the capsular ring, at least a portion of the anterior and posterior surfaces being substantially flat. The capsular ring further includes an exterior surface extending around the circumference of the capsular ring between the anterior surface and the posterior surface, wherein there is a sharp transition between the exterior surface and both the anterior surface and the posterior surface. The capsular ring further includes a plurality of orifices spaced circumferentially around the exterior surface and a plurality of haptics spaced circumferentially around the exterior surface and extending outwardly from the capsular ring; each of the plurality of haptics being configured, upon insertion of the capsular ring into a capsular bag of a patient's eye, to engage an equatorial region of the capsular bag of the patient's eye.

Certain embodiments of the present disclosure may provide one or more technical advantages. For example, the addition of haptics to the capsular ring may provide for better centration of the ring in the capsular bag. Additionally, the haptics may promote even stretching of the capsular bag, and that even stretching may increase contact between the capsular bag and the capsular ring (on both the anterior and posterior sides of the capsular ring). Increased contact between the capsular bag and the capsular ring may help prevent migration of lens epithelial cells, thereby mitigating PCO.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIGS. 4A-4B illustrate another alternative capsular ring, according to certain embodiments of the present disclosure;

Figure 1:
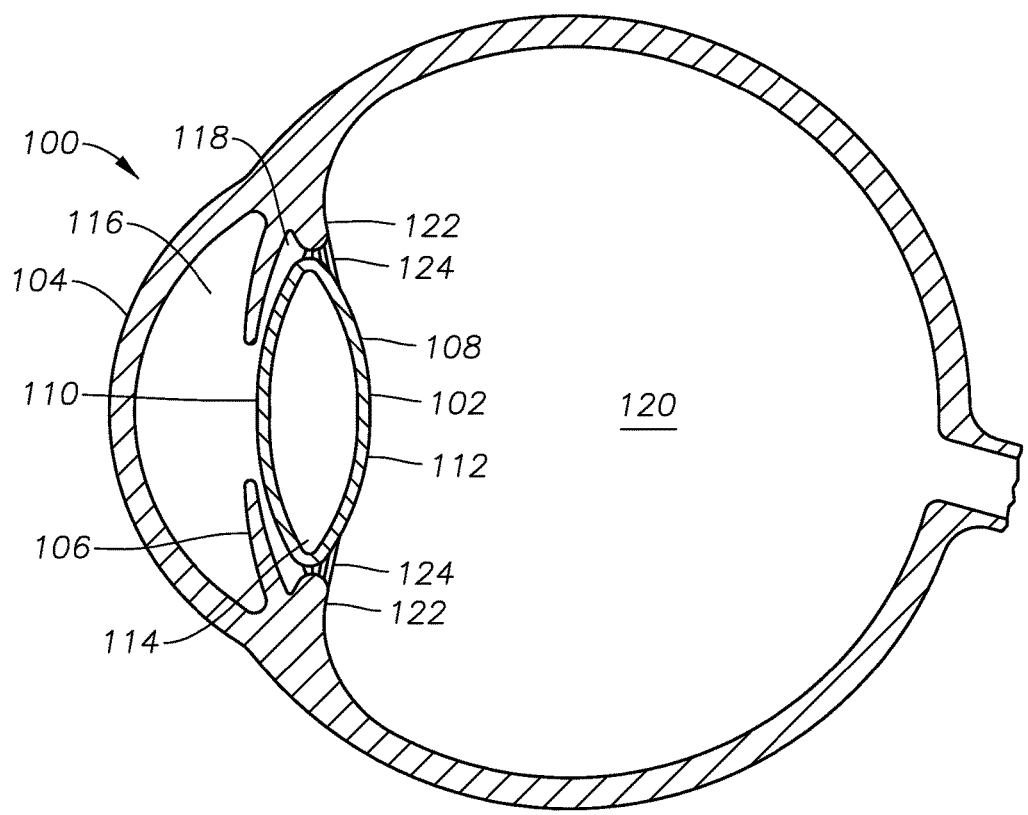
FIG. 1 is a diagram of an eye illustrating anatomical structures related to the surgical removal of a cataract and the implantation of an IOL.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

Figure 2A:
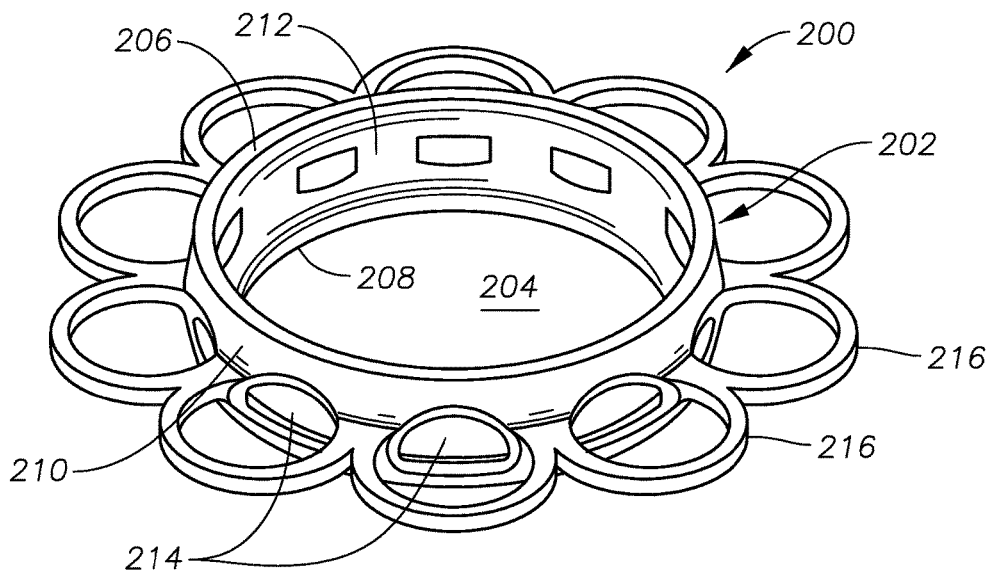
FIGS. 2A-2B illustrate an exemplary capsular ring 200, according to certain embodiments of the present disclosure.
Figure 2B:
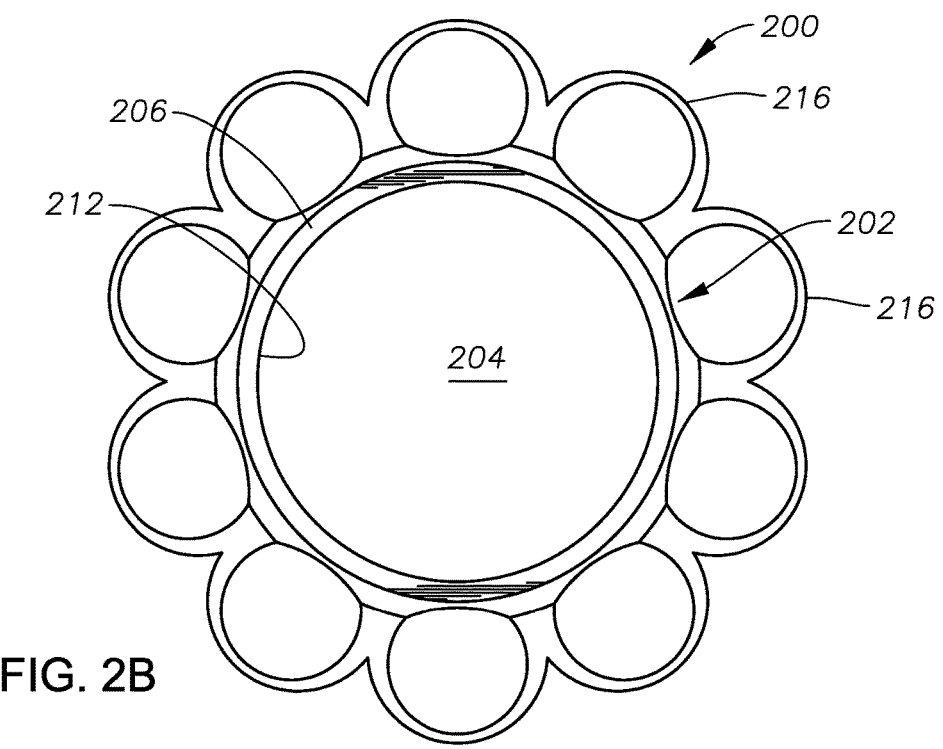

In general, the present disclosure relates to an IOL system including a capsular ring designed to improve centration of the capsular ring in the capsular bag 108 as well as inhibit PCO. In certain embodiments, a capsular ring includes a plurality of circumferentially spaced haptics extending outwardly from the capsular ring. The circumferentially spaced haptics may stretch the capsular bag 108 by engaging an equatorial region bag, helping to center the capsular ring in the bag. Additionally, by stretching the capsular bag 108, the capsular ring may inhibit PCO by increasing contact between the capsular bag and the anterior/posterior surfaces of the ring FIGS. 2A-2B illustrate an exemplary capsular ring 200, according to certain embodiments of the present disclosure. Capsular ring 200 comprises a flexible member 202 that, when in the depicted expanded (i.e., unstressed) position, defines a generally circular central opening 204. Capsular ring 200 may be defined by an anterior surface 206 and a posterior surface 208, and anterior surface 206 and posterior surface 208 may be connected on one side by an exterior surface 210 and on the other side by an interior surface 212. In other words, anterior surface 206, posterior surface 208, exterior surface 210, and interior surface 212 may collectively define the cross-sectional shape of capsular ring 200. As used herein, the terms "anterior" and "posterior" refer to the positioning of the surfaces after capsular ring 200 has been inserted into the capsular bag 108 of a patient's eye. However, because capsular ring 200 may be symmetrical (i.e., in cross section, anterior surface 206 may mirror posterior surface 208 about a center line of capsular ring 200), a particular orientation within the capsular bag 108 may not be necessary.

Capsular ring 200 may be shaped and configured to expand the capsular bag 108 of a patient's eye so as to prevent the anterior capsule 110 from contacting the posterior capsule 112 and allow the free circulation of aqueous humor within the capsular bag 108, both of which may inhibit lens epithelial cell proliferation. In certain embodiments, exterior surface 210 may be curved outward, defining a generally convex surface. The shape of the convex outer surface 210 may generally correspond to the shape of the capsular bag 108 at its equatorial region 114 in order to promote good contact between the capsular ring 200 and the anterior capsule 110/posterior capsule 112. In certain embodiments, interior surface 212 may be concave, and the curvature of the interior surface 212 may substantially match that of exterior surface 210. The concave shape of the interior surface 212 may be sized such that it may receive edges or portions (e.g., haptics) of an IOL such that an IOL may be centered within capsular ring 200.

Although exterior surface 210 and interior surface 212 are depicted and described as being convex and concave, respectively, the present disclosure contemplates that exterior surface 210 and interior surface 212 may each comprise any suitable shape, according to particular needs. As one example, exterior surface 210 may comprise a concave surface such that when implanted in the capsular bag, an equatorial void is created along equatorial region 114. As another example, interior surface 212 may comprise a square or rectangular shaped region configured to receive a haptic of a lens portion of the IOL having a corresponding shape.

In certain embodiments, capsular ring 200 may comprise a plurality of orifices 214 disposed circumferentially on the periphery of the capsular ring 200. Orifices 214 may help promote the above-described free circulation of aqueous humor within the capsular bag 108, which may inhibit lens epithelial cell proliferation. Additionally, orifices 214 may lower the overall volume of the capsular ring 200, which may increase the flexibility, contractibility, and expandability of the capsular ring 200 (allowing for easier implantation, as described further below). Still further, orifices 214 may allow for existing IOLs (e.g., IOLs with open loop designs) to be used in conjunction with capsular ring 200 by extending each of the haptics of the IOL through one of the orifices 214.

In the pictured embodiment, the capsular ring 200 includes ten ovoid or oblong orifices 214 arranged in a symmetrical pattern around capsular ring 200. However, the present disclosure contemplates that capsular ring 200 may include any number and arrangement of orifices 214 having any suitable shape that allows for adequate flow of aqueous humor through capsular ring 200. For example, the orifices may consist of multiple, small holes forming a mesh-like configuration and/or may be unevenly spaced apart along capsular ring 200. Moreover, the number and arrangement of the orifices 214 may be selected in consideration of, among other factors, the type of condition to be treated, the patient's particular anatomy, or the type of IOL to be placed within the capsular ring.

In certain embodiments, capsular ring 200 may include a plurality of haptics 216. Haptics 216 may be deformable members extending outwardly from exterior surface 210 such that, when implanted in the capsular bag 108, they engage equatorial region 114. By engaging equatorial region 114, haptics 216 may serve to stretch the capsular bag 108, which may increase contact between (1) the anterior capsule 110 and anterior surface 206, and (2) posterior capsule 112 and posterior surface 208. In certain embodiments, anterior surface 206 and posterior surface 208 may each be generally flat surfaces having a sharp transition to exterior surface 210. Increased contact with these generally flat surfaces, when coupled with the sharp transition to exterior surface 210, may help create a barrier to lens epithelial cell migration (thereby mitigating PCO). Stretching the capsular bag 108 in the manner discussed above may additionally help maintain the capsular ring 200 in the proper position (centered within capsular bag 108)

Capsular ring 200 may include any suitable number of haptics 216 having any suitable shape for engaging capsular bag 108 in the manner discussed above. For example, as depicted in FIGS. 2A-2B, haptics 216 may each have a generally circular closed loop design with two points of contact with exterior surface 210. In certain embodiments, the number of haptics 216 may correspond to the number of orifices 214, and the two points of contact of each haptic 216 may straddle a corresponding orifice 214.

Figure 3A:
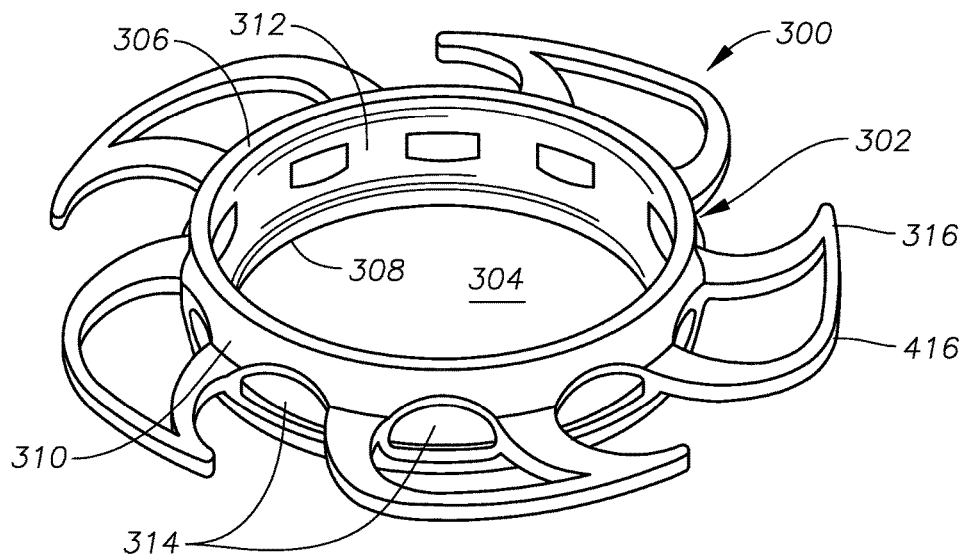
FIGS. 3A-3B illustrate an alternative capsular ring, according to certain embodiments of the present disclosure.
Figure 3B:
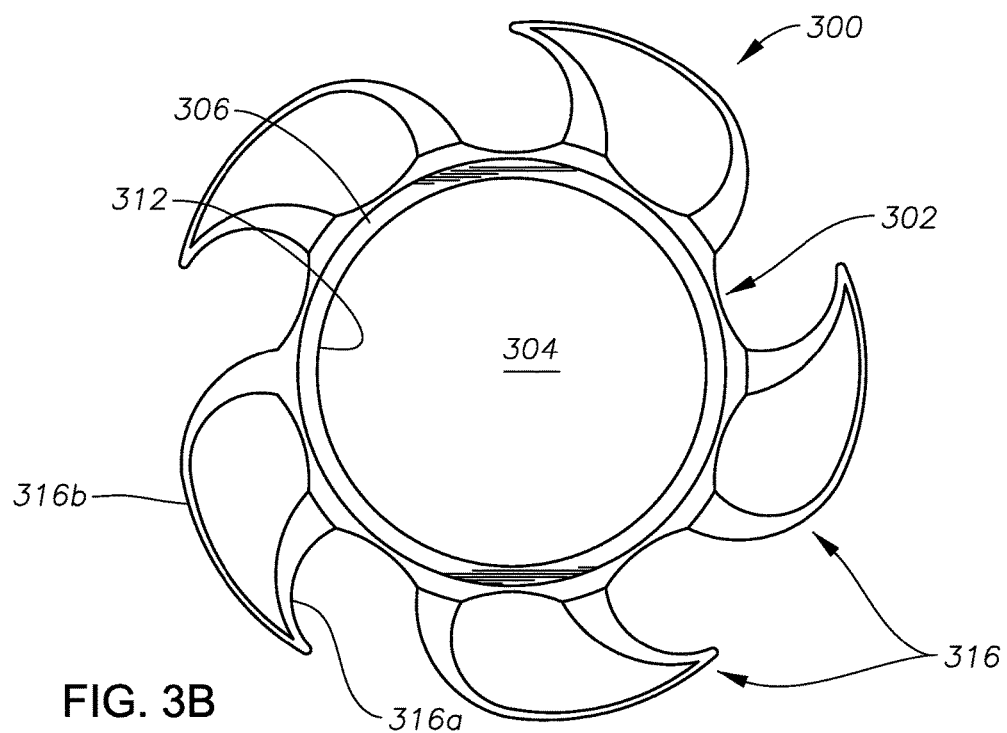

FIGS. 3A-3B illustrate an alternative capsular ring 300, according to certain embodiments of the present disclosure. Other than the number and shape of haptics 316 (described below), capsular ring 300 may be substantially the same as capsular ring 200 described above. Like haptics 216 of capsular ring 200, haptics 316 of capsular ring 300 may each have two points of contact with exterior surface 310, and those two points of contact may straddle a corresponding orifice 314. Additionally, rather than being substantially circular, haptics 316 may comprise two curved haptic members (316a and 316b) connected at one end to the exterior surface 310 (the two points of contact) connected at the other end to one another. In certain embodiments, capsular ring 300 may only have half the number of haptics 316 as orifices 314 such that only every other orifice 314 has a corresponding haptic 316.

FIGS. 4A-4B illustrate another alternative capsular ring 400, according to certain embodiments of the present disclosure. Other than the shape of haptics 416 (described below), capsular ring 400 may be substantially the same as capsular ring 200 described above. Unlike the above described haptics 216/316, haptics 416 of capsular ring 400 may each have a single point of contact with exterior surface 410. Moreover, the number of haptics 416 may correspond to the number of orifices 414, and each haptic may extend outwardly from exterior surface 410 at a location between orifices 414. Additionally, each haptic 416 may have a curved shape that decreases in width with distance from outer surface 410, as illustrated.

Although capsular rings 200, 300, and 400 are depicted having particular haptics 216, 316, and 416 are illustrated for exemplary purposes, the present disclosure contemplates that a capsular ring may have any suitable number of haptics having any suitable shape, according to particular needs.

The above-described capsular rings may be constructed from a structurally deformable biocompatible material or combination of such materials, enabling capsular rings to elastically or plastically deform without compromising its integrity. For example, the capsular rings may be made from a self-expanding biocompatible material, such as Nitinol. As another example, the capsular rings may be made from a resilient polymer, such as silicone or 2-phenyl ethyl acrylate and 2-pheylethyl methacrylate known under the name Acry-Sof®. As yet another example, the capsular rings may be made from an elastically compressed spring temper biocompatible material. Other materials having shape memory characteristics may also be used. In certain embodiments, the material composition of capsular rings resiliently biases the ring toward the expanded condition.

Figure 5:
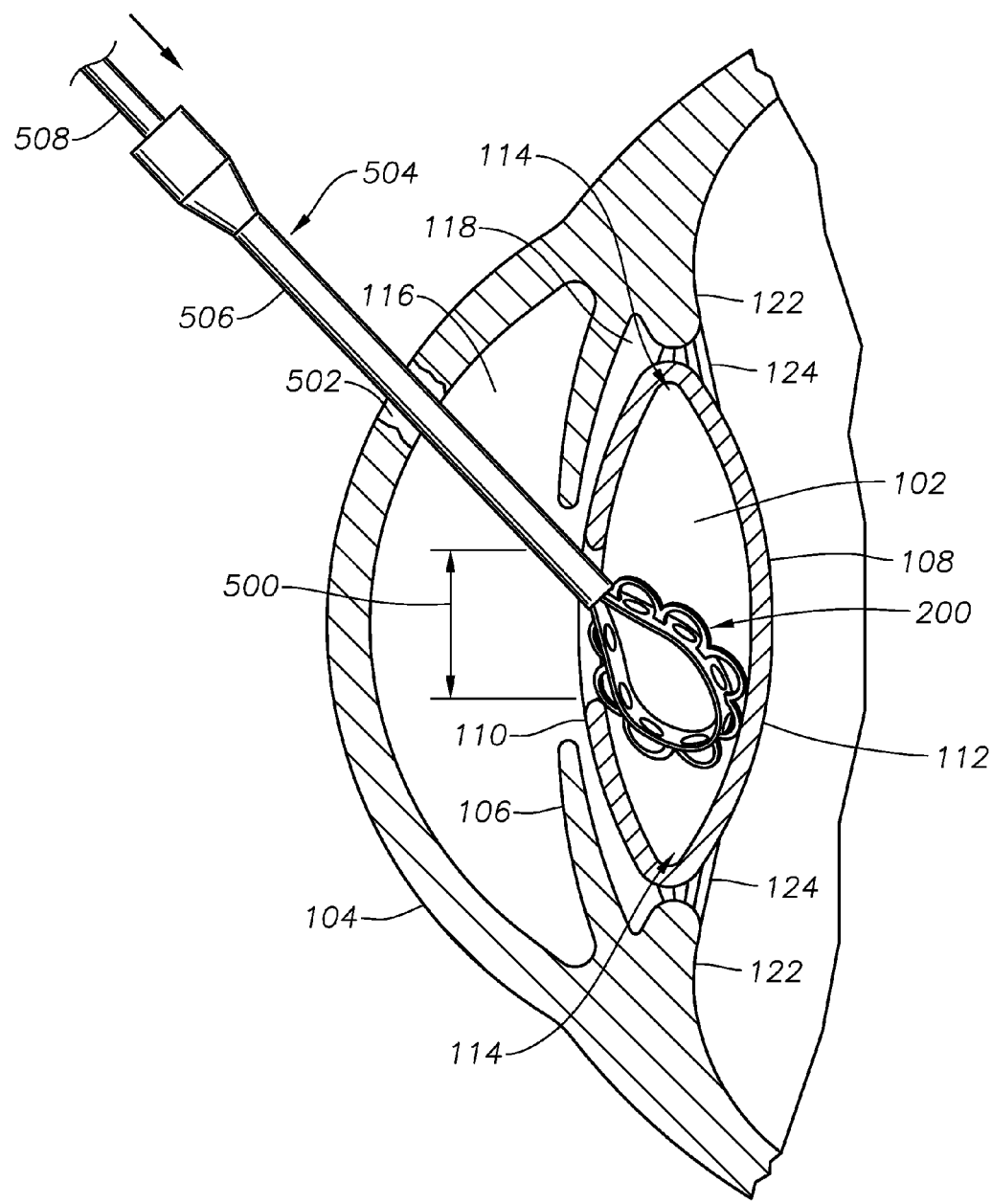
FIG. 5 illustrates an example mechanism for inserting the capsular ring depicted in FIGS. 2A-2B into the capsular bag of a patient's eye, according to certain embodiments of the present disclosure.

The above-discussed structurally deformable materials may allow capsular rings to be restrained in a low profile configuration during delivery into the eye and to resume and maintain its expanded shape in vivo after the delivery process. For example, FIG. 5 illustrates an example mechanism for inserting capsular ring 200 into the capsular bag 108 of a patient's eye 100, according to certain embodiments of the present disclosure. The capsular bag 108 of eye 100 is shown with an anterior capsulorhexis 500 (i.e., an area of the anterior capsule 110 that has been removed) and with the natural lens removed. As a result, an incision 502 in the cornea 104 may allow for the insertion of capsular ring 200 into capsular bag 108 via incision 502 and anterior capsulorhexis 500.

In certain embodiments, capsular ring 200 may be inserted into the capsular bag 108 of a patient's eye 100 using a delivery instrument 504. A lumen 506 of delivery instrument 504 may be inserted through corneal incision 502 (e.g., a 1.8-4 mm incision), through anterior capsulorhexis 500, and into the capsular bag 108. Capsular ring 200 may be housed in the lumen 506 in a compressed (i.e., unexpanded) state. Delivery instrument 504 may include a plunger 508 configured to translate longitudinally within lumen 506 such that plunger 508 may push capsular ring 200 out of the distal end of lumen 506 and into capsular bag 108. Upon exiting the distal end of lumen 506 of delivery instrument 504, capsular ring 200 may assume the expanded position and may be located along the equatorial region 114 of capsular bag 108.

Although a particular technique for inserting capsular ring 200 into the capsular bag 108 of a patient's eye 100 has been described, the present disclosure contemplates that capsular ring 200 may be inserted into the capsular bag 108 of a patient's eye 100 using any suitable technique, according to particular needs.

Figure 6:
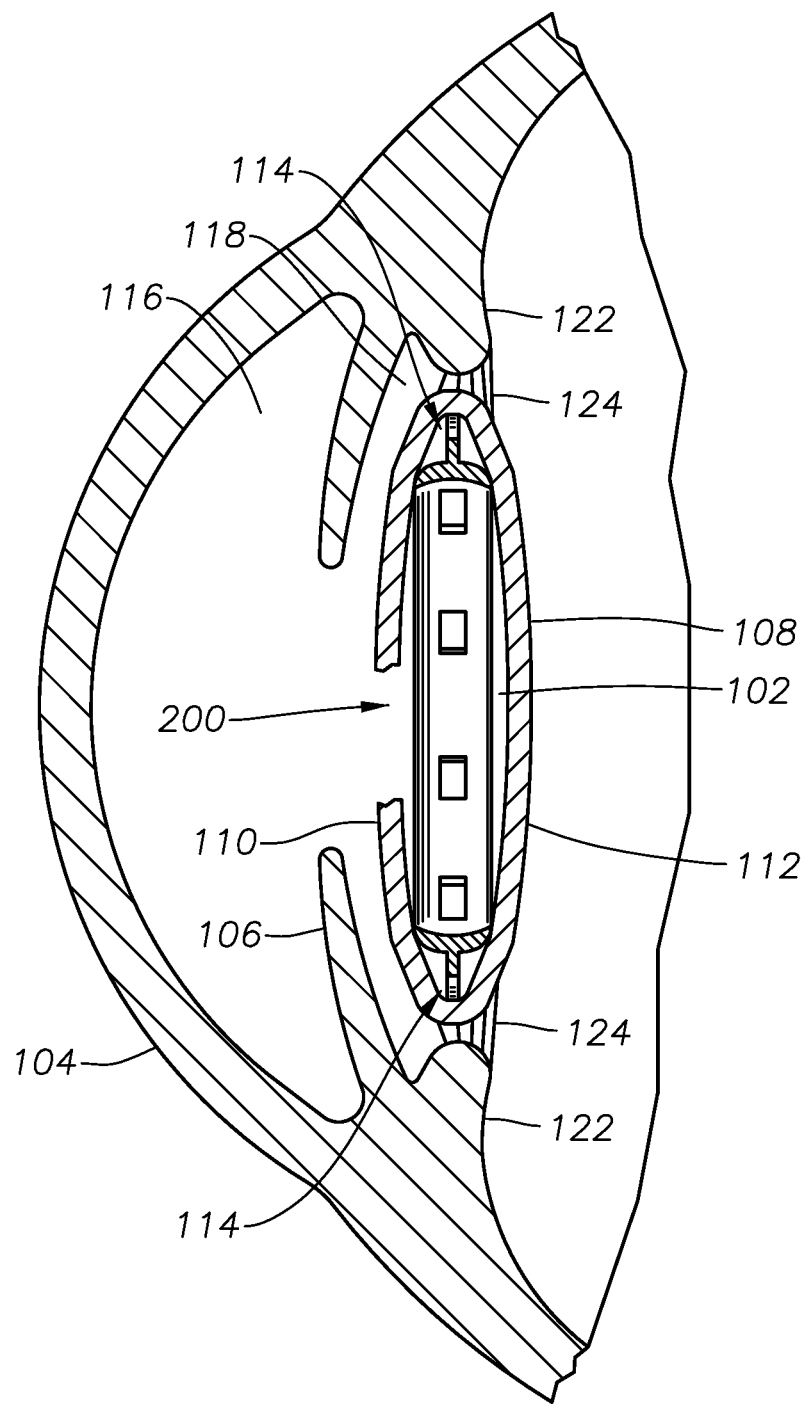
FIG. 6 illustrates a cross-section of the capsular ring depicted in FIGS. 2A-2B after insertion into the capsular bag of a patient's eye, according to certain embodiments of the present disclosure.

FIG. 6 illustrates a cross-section of capsular ring 200 after insertion into the capsular bag 108 of a patient's eye 100, according to certain embodiments of the present disclosure. When positioned along the equatorial region 114 of capsular bag 108, haptics 216 may engage the equatorial region 114 and stretch capsular bag 108. The capsular ring 200 may maintain separation between anterior capsule 110 and posterior capsule 112 (i.e., capsular ring 200 may keep capsular bag 108 open), and the stretching of capsular bag 108 may increase contact between the anterior capsule 110 and posterior capsule 112 and the surfaces 206/208 of the capsular ring 200. Because capsular bag 108 is open, aqueous humor located in the anterior chamber 116 may be allowed to circulate into capsular bag 108 by passing through anterior capsulorhexis 300 and into equatorial region 114 via orifices 214. This circulation may help to prevent migration of lens epithelial cells, thus reducing the likelihood of PCO.

Additionally, the increased contact between surfaces 206/208 of the capsular ring 200 due to the stretching of capsular bag 108, when coupled with the sharp edges of those surfaces, may help prevent migration of lens epithelial cells from equatorial region 114. This may further help to reduce the likelihood of PCO.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A capsular ring for insertion into a capsular bag of a patient's eye, the capsular ring comprising:
   a substantially circular anterior surface defining a central void of the capsular ring, at least a portion of the anterior surface being substantially flat;
   a substantially circular posterior surface defining the central void of the capsular ring, at least a portion of the posterior surface being substantially flat;
   an exterior surface extending around the circumference of the capsular ring between the anterior surface and the posterior surface, wherein there is a sharp transition between the exterior surface and both the anterior surface and the posterior surface;
   at least four orifices evenly spaced circumferentially around the exterior surface and extending through the capsular ring and into the central void;
   at least four closed loop haptics each having two points of connection with the exterior surface, the two points of connection for each closed loop haptic being located on either side of a corresponding one of the orifices, wherein each of the plurality of haptics is configured, upon insertion of the capsular ring into a capsular bag of a patient's eye, to engage an equatorial region of the capsular bag of the patient's eye.

2. The capsular ring of claim 1, wherein at least a portion of the capsular ring is constructed from a self-expanding, biocompatible material.

3. The capsular ring of claim 1, wherein the exterior surface comprises of convex surface.

4. The capsular ring of claim 1, further comprising an interior surface extending between the anterior surface of the capsular ring and the posterior surface of the capsular ring, the interior surface configured such that one or more haptics of a lens may engage the interior surface.

5. The capsular ring of claim 1, wherein each of the plurality of orifices are ovoid in shape.

* * * * *